United States Patent [19]

Yoshida

[11] 4,379,636

[45] Apr. 12, 1983

[54] INSPECTION DEVICE

[75] Inventor: Hajime Yoshida, Tokyo, Japan

[73] Assignee: Hajime Industries Ltd., Tokyo, Japan

[21] Appl. No.: 190,712

[22] Filed: Sep. 25, 1980

[30] Foreign Application Priority Data

Oct. 18, 1979 [JP] Japan .................................. 54-134502

[51] Int. Cl.³ .............................................. G01J 3/50
[52] U.S. Cl. .................................... 356/407; 209/524; 209/582; 250/226
[58] Field of Search ............... 356/407, 416, 419, 425; 209/580–582, 524; 250/226

[56] References Cited

U.S. PATENT DOCUMENTS

| | | | |
|---|---|---|---|
| 3,980,181 | 9/1976 | Hoover et al. | 209/582 X |
| 4,011,016 | 3/1977 | Layne et al. | 356/425 X |
| 4,205,752 | 6/1980 | Malvick et al. | 209/582 X |

*Primary Examiner*—F. L. Evans
*Attorney, Agent, or Firm*—Murray Schaffer

[57] ABSTRACT

An inspection device is disclosed which includes a color sensor which has a plurality of photoelectric conversion elements each being responsive to respective different wave lengths of light from an object to be inspected and producing an electrical signal, a zero balance setter which processes the output signal from the color sensor and then takes a zero balance, a tolerance range setter which receives the output of the zero balance setter and produces an abnormal signal in conjunction to a tolerance range of the object to be inspected, a detector which produces an electrical signal to notify when the object arrives at a predetermined location; and a detection location timing section which passes the output of the tolerance range setter by the output signal from the detector.

7 Claims, 12 Drawing Figures

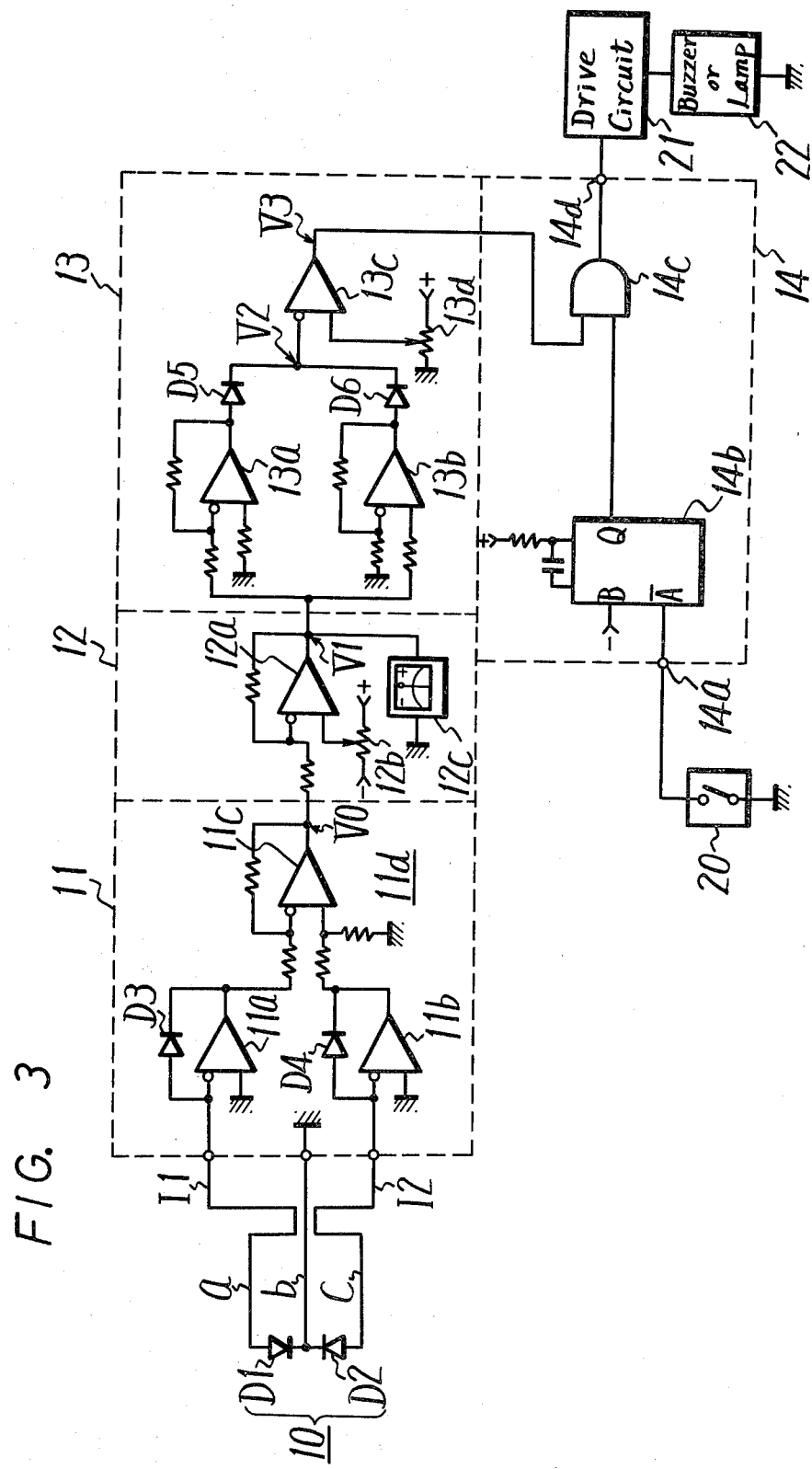
F/G. 3

INSPECTION DEVICE

BACKGROUND OF THE INVENTION

1. Field of the Invention

The present invention relates generally to an inspection device, and is directed more particularly to a defect inspection device which can inspect the defects of a broad range, especially including the existence of objects, positioning distortion of labels or the like which adhere on the objects, or color differences on the objects and other means.

2. Description of the Prior Art

Many types of inspection devices are conventionally proposed to inspect the defects on objects by utilizing a photo diode or the like, but such conventional defect inspection devices for object utilize the strength of light incident on one photo diode, in which a threshold value for the brightness of the light is set to thereby detect the defects on objects to be inspected. Accordingly, by the defect inspection devices under the prior art, it was practically impossible to inspect shapes, posture or designs of objects in many variations, complications as well as delicacy.

Further, by the defect inspection devices under the prior art, it was practically impossible to inspect portions of objects which irradiate lights of different colors.

OBJECTS AND SUMMARY OF THE INVENTION

Accordingly, an object of the present invention is to provide an inspection device for objects by which the inspection of defects on objects for a wide range can be conducted.

Another object of the present invention is to provide an inspection device which can surely and adequately inspect objects even though the objects to be inspected may irradiate lights with different wave lengths (colors).

According to an aspect of the present invention, an inspection device is proposed which comprises:

- a color sensor means which has one body of photoelectric conversion elements, each being responsive to respective different wave lengths of light from an object to be inspected and producing an electrical signal;
- a zero balance setting means which processes the output signal from said color sensor means and then takes a zero balance;
- a tolerance range setting means which receives an output of said zero balance setting means and produces an abnormal signal in conjunction to a tolerance range of said object to be inspected;
- a detector means which produces an electrical signal to notify when said object arrives at a specified location; and
- a detection location timing means which passes the output of said tolerance range setting means by the output signal from said detector means.

The additional, and other objects, features and advantages of the present invention will become apparent from the following description taken in conjunction with the accompanying drawings through which the like references designate the same elements and parts.

BRIEF DESCRIPTION OF THE DRAWINGS

FIG. 3 is a systematic circuit diagram showing an example of the present invention;

DESCRIPTION OF THE PREFERRED EMBODIMENTS

The present invention with features as above mentioned will be explained hereunder in reference with the drawings.

Figure 1A:
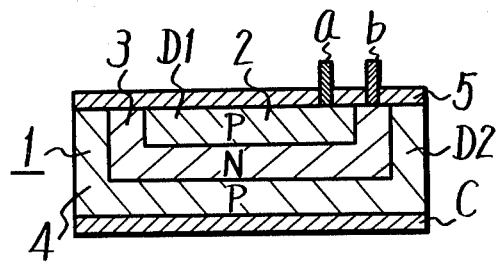
FIG. 1A is a cross-sectional view showing an example of a color sensor used under the present invention.
Figure 1B:
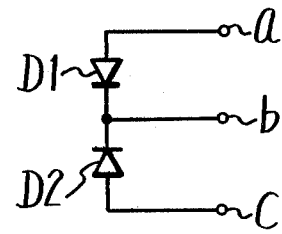
FIG. 1B is an equivalent circuit of the color sensor shown in FIG. 1A.
Figure 5:
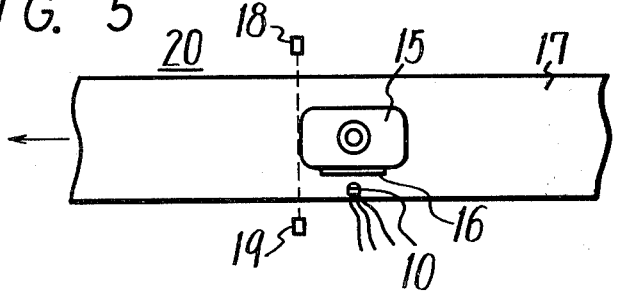
FIG. 5 is a schematic diagram showing an object to be inspected under the present invention as well as its surrounding.

First, an example of a color sensor utilized for the present invention will be explained in reference with FIG. 1. This shows a semiconductor color sensor which is sold on the market presently, which is constructed as shown on FIG. 1A whereas, on one semiconductor substrate (such as silicon substrate) 1 going down from the upper surface to the lower surface thereof, a P-type layer 2, an N-type layer 3 and a P-type layer 4 are formed in sequence, whereby two PN-junctions and hence two photo diodes D1 and D2 are formed therein. In FIG. 1A, 5 is an electrical insulation cover layer which is substantially transparent and coated on the surface of the semiconductor substrate 1, a and c are one electrode of the respective photo diodes D1 and D2, and b is the other common electrode for both diodes D1 and D2. Therefore, an equivalent circuit of the color sensor shown in FIG. 1A becomes as shown on FIG. 1B.

The semiconductor color sensor as shown on FIG. 1 functions as follows. For instance, a short wave length light such as blue color shade is mainly absorbed by a portion of the semiconductor substrate 1 near the surface thereof while the long wave length such as red color shade pass through the surface portion of the semiconductor substrate 1 and are mainly absorbed by the deep portion of the semiconductor substrate 1. In other words, the thickness of the substrate 1 of the semiconductor color sensor functions as an optical filter, by which the upper or the shallow side photo diode D1 of the color sensor is highly sensitive to lights of short wave lengths while the photo diode D2 which is at the bottom or the deep side of the color sensor is highly sensitive to lights with long wave lengths. This is shown by the wave length versus sensitivity characteristic graph on FIG. 2 in which curves A and B respectively correspond to the photo diodes D1 and D2.

Such curves A and B change in response to the characteristics of the substrate 1.

FIG. 3 is a systematic diagram showing an example of the circuit construction of the inspection device under the present invention. On the drawing, 10 is the color sensor which consists of two photo diodes D1 and D2 as shown on FIG. 1. Output currents I1 and I2 from photo diodes D1 and D2 which respectively respond to different wave lengths of light, for instance, two types of different wave length lights that reach color sensor 10, are fed through electrodes a, b and c to a light wave length detector 11 which detects the wave lengths of the light incident on the color sensor 10 and which includes operational amplifiers 11a, 11b and 11c, and diodes D3 and D4. In other words, the current I1, which responds to the short wave length light, for example, blue color light and is obtained from photo diode D1 is fed to the operational amplifier 11a as well as diode D3, while the current I2, which responds to the long wave length light such as red color light and is obtained from photo diode D2, fed to the operational amplifier 11b as well as diode D4. Both currents I1 and I2 are logarithm-compressed therein, respectively, and then they are supplied to a subtractor circuit 11d, which mainly consists of the operational amplifier 11c etc., at where they are subtracted from one another to provide an output voltage of V0. This output voltage V0 from the light wave length detector 11 is expressed as follows.

$$V0 \propto \log I2 - \log I1 = \log (I2/I1) \quad (1)$$

Figure 2:
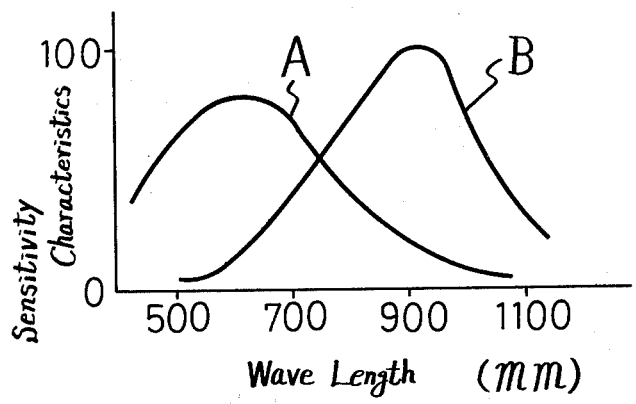
FIG. 2 is a graph showing the characteristic of the color sensor as shown on FIG. 1.
Figure 4:
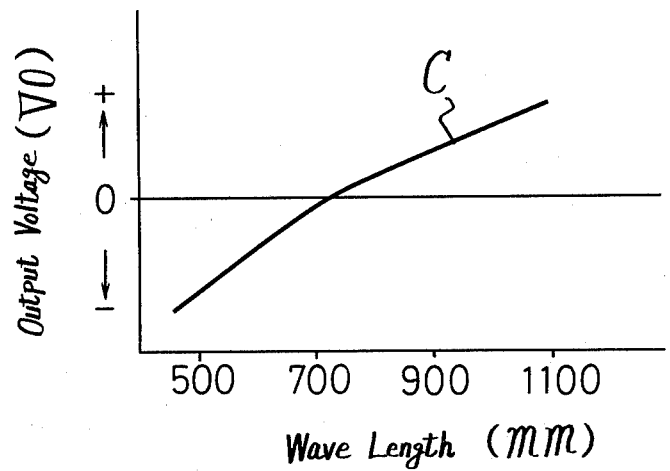
FIG. 4 is a graph showing the output characteristic of a portion of the circuit as shown on FIG. 3.

As apparent by the characteristic graph of FIG. 2, the ratio I2/I1 is constant regardless of the strength variation in the incident light on color sensor 10, so that it will be apparent from the equation (1) that the output voltage V0 from the light wave length detector 11 does not vary against the strength variation in the incoming light to color sensor 10. Accordingly, the output voltage V0 varies in conjunction with the ratio among the wave length components of light contained in the incident light on colour sensor 10, and the relation between the voltage V0 and the wave length of the incident light varies as shown by a curve C on FIG. 4. In other words, depending upon the ratio among the wave length components of the incident light, voltage V0 varies either to the plus side + or to the minus side −, accordingly.

As shown on FIG. 3, the output voltage V0 from the light wave length detector 11 is applied to a zero balance setter 12 provided at the next stage. This zero balance setter 12 consists of an operational amplifier 12a as well as an adjustor 12b such as a variable resistor or the like. The output voltage V0 from the light wave length detector 11 is fed to one input terminal of operational amplifier 12a, while the other input terminal thereof is supplied with the voltage from the adjustor 12b as will be hereafter described. At the zero balance setter 12, adjustor 12b is adjusted so that the output voltage V1 from operational amplifier 12a becomes zero at the starting point of the inspection as will be later described. As shown on the graph of FIG. 4, since output voltage V0 from the light wave length detector 11 changes from the minus side − to the plus side + in response to the composition ratio of the wave lengths (light colors) contained in the incident light on color sensor 10, at the later described inspection, to the output voltage V0 of the light wave length detector 11 which responds to the constant or standard color composition ratio of the light within the visual field of color sensor 10, adjustor 12b is adjusted (zero balanced) so that the output voltage V1 from the zero balance setter 12 becomes zero. In other words, whether the output voltage V0 from the light wave length detector 11, that responds to the standard color composition ratio of light within the visual field of color sensor 10, is on the minus side or on the plus side, adjustor 12b is adjusted so that the output voltage V1 of the zero balance setter 12 becomes zero. This means that the zero balance setter 12 is set to the standard color composition ratio of the light in the visual field of color sensor 10. Further, in order to confirm that zero balance has been taken in zero balance setter 12 or not, a voltage meter 12c with a zero center dial is connected to the output side of operational amplifier 12a. If the needle of this voltage meter 12c points zero, it is known that the above mentioned zero balance has been taken. In such respect, many other means and methods may be obviously considered.

With the condition that output voltage V1 of the zero balance setter 12 is set at zero, if an object is sensed by color sensor 10, whenever the color composition ratio of the light from the object within the visual field of the color sensor 10 is other than the already adjusted color composition ratio, output voltage V0 of the light wave length detector 11 will deviate to the minus or the plus side compared to the previously set up. Therefore, the output voltage of the zero balance setter 12, in other words, the output voltage V1 of operational amplifier 12a becomes not zero but deviates to the minus or plus side.

At the next stage of the zero balance setter 12, a tolerance range setter 13, which includes operational amplifiers 13a, 13b, diodes D5 and D6, comparator 13c and so on, is placed whereas the output voltage V1 from the zero balance setter 12 is fed to operational amplifiers 13a and 13b. In this case, the connections of operational amplifiers 13a and 13b are selected as follows. When the output voltage V1 of the zero balance setter 12 deviates to the plus or minus side from zero, both operational amplifiers 13a and 13b deliver outputs as the deviation result of, for example, plus side. The plus side outputs only of operational amplifiers 13a and 13b are taken out through diodes D5 and D6 connected at the output rides of operational amplifiers 13a and 13b. The outputs of both diodes D5 and D6 are taken in common (as voltage V2) and supplied to one input terminal of the comparator 13c. To the other input terminal of comparator 13c, a voltage adjustment means such as a sweeper or movable piece of a variable resister 13d is connected, so that the voltage applied to the other input terminal of the comparator 13c can be selected desirably. At this comparator 13c, whenever a voltage higher than the voltage set by the variable resister 13d is applied to the one input terminal thereof, output signal V3 is generated therefrom. Accordingly, if the set voltage by the variable resister 13d is selected large, the comparator 13c will not deliver output signal V3, unless a considerably large deviation is voltage V2 from the established zero at the zero balance setter 12 occurs. Therefore, even a large tolerance can be arranged. This difference of tolerance range can be matched to the later described actual inspection standards which is conducted by adjustment of the variable resister 13d.

At the later stage to the tolerance range setter 13, a detection location timing section 14 is provided. The function thereof is to specify or restrict the input from the color sensor 10 within a certain specified time by an external trigger signal. For instance, as shown on FIG.

5, upon inspecting the existence of a label 16 or whether positioning thereof is proper or not on an inspected object such as a bottle 15 while the bottle 15 is flowing on belt conveyer 17, a location detection device 20, which for instance consists of a light emission element 18 such as an LED and a photo electric conversion element 19 such as a photo diode, is placed at a given location (detection location) in relation with belt conveyer 17. Thus, when the bottle 15 arrives at the detection location, the above trigger signal is delivered from location detection device 20. Normally, photo diode 19 receives the light from light emission element 18, but when the bottle 15 arrives at the given location, the light from the light emission element 18 to the photo diode 19 is shielded by the bottle 15, at which time the trigger signal is output from photo diode 19, which is fed to an input terminal 14a of the detection location timing section 14 as shown on FIG. 3. This input terminal 14a is connected to an input terminal $\overline{A}$ of one-shot multivibrator 14b, for instance, which specifies the detection function timing or time period, so that when the trigger signal is fed to input terminal $\overline{A}$ of the one-shot multivibrator 14b through input terminal 14a, the vibrator 14b supplies a pulse with a short time width such as few micro seconds, for instance, to one input terminal of AND circuit 14c. The time width of the output pulse of multivibrator 14b is selected within a range so that even though the object 15 to be inspected is moving at high speed, no influence is caused to the inspection thereof. Normally, this time width of the output pulse is, as above mentioned, within few micro seconds and it practically does not create any problem for inspection. To the other input terminal of the AND circuit 14c, output V3 from the tolerance range setter 13 is supplied. Needless to say, the color sensor 10 is arranged as shown on FIG. 5 so that when the inspected object, which is the bottle 15, arrives at the given location (detection location), the portion to be inspected of the bottle 15, for instance, a certain portion of the label 16 comes within the visual field of color sensor 10.

When bottle 15 arrives at the inspection location, the trigger signal is supplied to one shot multivibrator 14b through the input terminal 14a from the location detection device 20, which then supplies the pulse with time width of few micro seconds as above mentioned to the AND circuit 14c. When voltage V2 which goes over the tolerance limit as established by the tolerance range setter 13 is generated (this is equivalent to the case where the bottle 15 which is the inspected object has a mispositioned label 16 and hence the bottle 15 is a defect product), the comparator 13c which receives such voltage V2 generates output signal V3 (as above mentioned this indicates that the inspected object is a defective product). This output signal V3 passes through AND circuit 14c and is delivered to output terminal 14d as a signal which indicates that the inspected object is abnormal or a defective product. Therefore, this output signal which indicates that the inspected object is abnormal or a defective product may be supplied to, for instance, a lamp or buzzer or the like to alarm that the inspected object is abnormal or a defective product, or it may be fed to a reject mechanism which functions to remove the defective bottle 15 from belt 17. The example of the invention shown on FIG. 3 is such an example in which an alarm is generated by the signal from output terminal 14d of the detection location timing section 14 fed to a buzzer or lamp 22 through a drive circuit 21. On the other hand, when the location detection device 20 outputs the trigger pulse, if the bottle 15, which arrives at the detection location as a specified, is a normal or good product, the voltage V2 at the tolerance range setter 13 is zero, or if not zero, within the tolerance range established by the comparator 13c and hence comparator 13c does not generate any output. Accordingly, at this time, the AND circuit 14c does not deliver any output. Therefore, no alarm of abnormal condition is made.

Figure 6A:
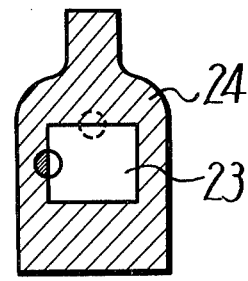
FIG. 6A is an enlarged side view of another example of the object to be inspected.
Figure 6B:
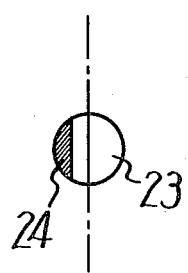
FIGS. 6B to 6D are respectively enlarged views of a part of FIG. 6A.
Figure 6C:
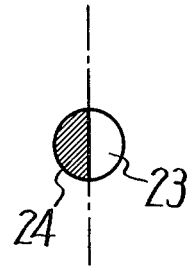
Figure 6D:
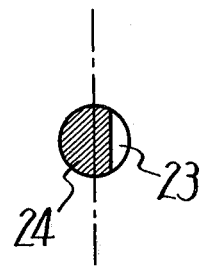

A case where an example of the present invention is applied to inspect whether or not a brown bottle is adhered with a white label at the correct position will be explained. FIG. 6A is a front view of a brown colored bottle 24 (shown by hatcher) on which a white label 23 is adhered. FIGS. 6B, 6C and 6D are each showing, in an enlarged scale, a portion to be inspected of the bottle 24 as shown in a circle on FIG. 6A, in other words, the visual field of color sensor 10. In this case, FIG. 6C is a case where the label 23 is placed in a normal or correct position (normal position in respect to the right and left directions), and FIGS. 6B and 6D respectively show cases where the label 23 is not placed in the normal position (in this case, mispositioned to the right and left directions).

Under the present invention, when the bottle 24 arrives at the inspection location, the color sensor 10 is just located so that its visual field correctly coincides with the inspected portion of bottle 24 as indicated with circle mark. When half of this circle mark portion of bottle 24 arriving at the detecting location is the same with the label 23 color white and the remaining half the same with a brown color of the bottle 24, in other words, as shown on FIG. 6C, when label 23 adhered to bottle 24 at the detecting location is at the standard or correct position, zero balance setter 12 takes the zero balance, and the tolerance range is set at a proper value by the setter 13, for instance, set at a value responding to a tolerable range (for instance, one milimeter) slide from the standard position of label 23. By the above arrangements, when the bottle 24 arriving at the inspection location bears the portion fallen in the visual field of color sensor 10 as shown in the circle mark which portion is, for instance, the portions as shown on FIGS. 6B and 6D, an output which indicates an abnormal condition is obtained at output terminal 14d and detection is made that the label 23 as adhered onto bottle 24 is not standard. Even in the case that the visual field of color sensor 10 is not as shown on FIG. 6C, but as shown on FIGS. 6B and 6D, if the mispositioning of label 23 is as above mentioned within the range of one milimeter, for instance, it falls within the tolerance range as set by comparator 13c and hence no output signal is obtained at output terminal 14d as a natural course.

Further, in the above example, although the right and left direction label mispositioning was detected by the present invention, it will be obvious that the vertical or up and down direction mispositioning can also be detected by fixing the visual field of color sensor 10 on a horizontal direction line of the label 23 (refer to the dot line circle on FIG. 6A).

It will be also apparent that other than detecting a combination of brown color and white color, any other desired color combination can be detected by the same color sensor.

Further, although the circuit example as shown on FIG. 3 of the present invention deals with each of the output signals mainly in analog manner, by utilizing an A/D converter, each output signal may be digitized and by a logic circuitry, a similar detection is obviously possible by any concern experienced in the art.

Now, an example of the above digital process circuit according to the present invention will be described with reference to FIG. 7 in which the reference same as those in FIG. 3 designate the same parts and elements so that their detailed explanation will be omitted.

Figure 7:
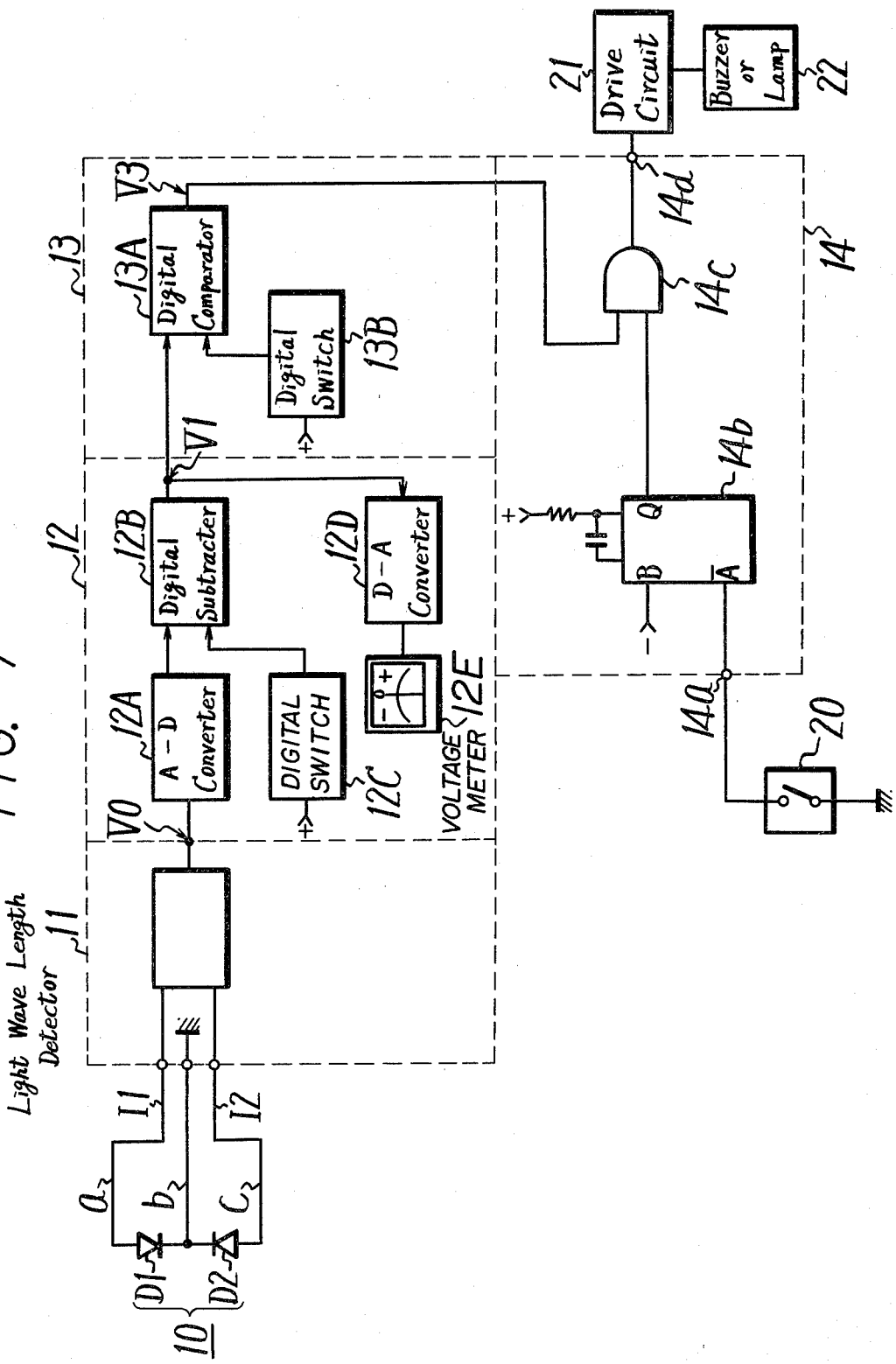
FIG. 7 is a systematic circuit diagram showing another example of the invention.

In the example of the invention shown in FIG. 7, the zero balance setter 12 includes an A-D converter 12A, a digital subtractor 12B, a digital switch 12C and a D-A converter 12D. The output voltage V0 from the light wave length detector 11, which is substantially same or that of FIG. 3 and hence shown by a single block in FIG. 7, is applied through the A-D converter 12A to one of the input terminals of digital subtracter 12B which is supplied with at its other input terminal with a predetermined bit set by the digital switch 12C which functions similar to the adjustor 12b of FIG. 3. The output V1 from the digital subtracter 12B, which corresponds to the operational amplifier 12a in FIG. 3, is fed through the D-A converter 12D to the meter 12E same as that of FIG. 3. Thus, when the subtracted output V1 from the digital subtracter 12B is zero or zero balance is set by adjusting the digital switch 12C, the pointer of the meter 12E points zero. Thus, it will be apparent that the elements 12B and 12C in FIG. 7 respectively correspond to the elements 12a and 12b in FIG. 3, and that both the zero balance setters in FIGS. 7 and 3 carry out substantially the same operation with each other and achieve the same effect.

The tolerance range setter 13 of FIG. 7 consists of a digital comparator 13A and a digital switch 13B. The output V1 from the digital subtracter 12B of zero balance setter 12 is applied to one of the input terminals of digital comparator 13A whose other input terminal is supplied with a predetermined bit which is selected by the digital switch 13B in consideration of the tolerance similar to the variable resistor 13d in the setter 13 of FIG. 3. Then, the digital comparator 13A produces an output V3, which corresponds to the voltage V3 in FIG. 3, when the output V1 is higher than the output set by the digital switch 13B. The output V3 from the digital comparator 13A is applied to the detection location timing section 14 which is same as that 14 of FIG. 3.

The other circuit construction of FIG. 7 is substantially same as that of FIG. 3 and also whole the operation of FIG. 7 is the same as that of FIG. 3, so that the description thereof will be omitted for the sake of brevity.

On the above examples of the present invention, a color sensor which has two photo diodes in one unit body is utilized, but it is possible by utilizing separate photo diodes to form a color sensor which has the same effect. For example, as shown on FIG. 8, two photo diodes D1 and D2 which are different is sensitivity to the wave length of light can be separately placed apart and the visual fields of the two are restricted to the same inspection portion on an object to be inspected (this is equivalent to the full line circle or dot line circle in FIG. 6A) to thereby form a color sensor 10'. In this case, circuitry which conducts the inspection to detect defects on the objects by processing the output of color sensor 10' can be exactly the same as those above explained example as shown on FIGS. 3 and 7 and detail explanations thereof will be omitted herein.

Figure 8:
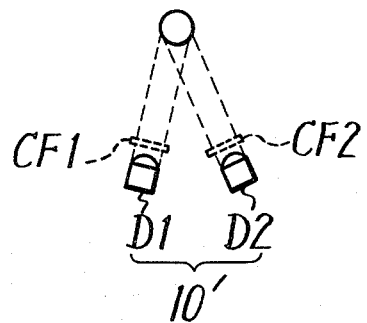
FIG. 8 is a sketch of another example of a color sensor utilized under the present invention.

In order to emphasize the response (sensitivity) to the different wave lengths or colors of lights by photo diodes D1 and D2, for instance, as shown in the broken lines on FIG. 8, color filters CF1 and CF2 which particularly respond to the colors of the inspected portion on the inspected object may be placed in front of photo diodes D1 and D2 respectively.

Further, it will be also apparent that a color sensor is formed by unitizing more than 3 photo diodes into one body or arranging separately, and by placing separate color filters different in color characteristics in front of each respectively, and that by proper modifications of each device at the later stage which processes the output from the color sensor unit as shown on FIG. 3 to match the number of outputs from the new sensor, the inspection of objects which is related with more than 3 different colours can be conducted.

Also, for inspections of words or designs of white color, for instance, on a transparent base, it is apparent that the present invention may be applied by irradiation of a bias light of a proper color thereto.

In addition, without escaping the scope of the novel concepts of the present invention, it is apparent that any concern skilled in the art may conduct many variations and changes, so that the scope of the invention should be determined by the appended claims only.

I claim as my invention:

1. An inspection device comprising:
   (a) a color sensor means having photoelectric conversion elements, each being responsive to respective different wave lengths of light from an object to be inspected and producing an electrical signal;
   (b) a light wave length detecting means for receiving the electrical signal from said color sensor means and for producing an output voltage which is varied to negative and positive sides in response to wave length component ratio of light incident from said object on said color sensor means;
   (c) a zero balance setting means which processes the output voltage from said light wave length detecting means and then takes a zero balance when a standard object is picked by said color sensor means;
   (d) a tolerance range setting means which receives an output of said zero balance setting means and produces an abnormal signal when the last mentioned output exceeds a predetermined tolerance range;
   (e) a location detection means which produces an electrical signal to notify when said object arrives at a predetermined location; and
   (f) a detection location timing means which receives the electrical signal from said location detection means, produces a pulse signal with a short time width and passes the output of said tolerance range setting means only when the output pulse signal appears.

2. An inspection device as claimed in claim 1, in which said color sensor means is a unitized body of at least two photo diodes as the photoelectric conversion elements which respectively respond to lights of at least two different colors.

3. An inspection device as claimed in claim 1, in which said color sensor means is a semiconductor color sensor which has a unitized body of at least two photo diodes as the photoelectric conversion elements which respectively respond to lights of at least two different colors.

4. An inspection device as claimed in claim 1, in which said color sensor means includes two photo diodes as the photoelectric conversion elements which are unitized as a single element.

5. An inspection device as claimed in claim 1, in which said color sensor means includes two photo diodes as the photoelectric conversion elements located a part with each other.

6. An inspection device comprising:
 (a) a color sensor means which contains at least two separate photo electric conversion elements which produce output electric signals respectively in response to light with at least two different wave lengths, said separate photo-electric conversion elements being respectively placed so that each of them has a visual field restricted to the same inspection area on an object to be inspected;
 (b) a light wave length detecting means for receiving the electrical signal from said color sensor means and producing an output voltage which is varied to negative and positive sides in response to wave length component ratio of light incident from said object on said color sensor means;
 (c) a zero balance setter means which processes the output signal from said light wave length detecting means to take a zero balance when a standard object is picked up by said color sensor means;
 (d) a tolerance range setter means which receives the output of said zero balance setter means and outputs an abnormal signal when the last-mentioned output exceeds a predetermined tolerance range;
 (e) a location detector means which outputs an electric signal to notify when said object arrives at a given location; and
 (f) a location detection timing section means which receives the electrical signal from said location detector means, produces a pulse signal with a short time width and passes the output of the said tolerance range setter means only when the output pulse signal appears.

7. An inspection device as claimed in claim 6, in which said photoelectric conversion elements of the color sensor respectively are construed by photo diodes with color filters in front of thereof.

* * * * *